(12) United States Patent
Takayama et al.

(10) Patent No.: US 11,141,234 B2
(45) Date of Patent: Oct. 12, 2021

(54) BENDING MECHANISM AND MEDICAL MANIPULATOR

(71) Applicant: OLYMPUS CORPORATION, Tokyo (JP)

(72) Inventors: Hiroyuki Takayama, Tokyo (JP); Noriaki Yamanaka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 251 days.

(21) Appl. No.: 16/417,728

(22) Filed: May 21, 2019

(65) Prior Publication Data
US 2019/0269473 A1 Sep. 5, 2019

Related U.S. Application Data

(63) Continuation of application No. PCT/JP2016/085313, filed on Nov. 29, 2016.

(51) Int. Cl.
| | |
|---|---|
| *A61B 34/00* | (2016.01) |
| *A61B 34/30* | (2016.01) |
| *B25J 18/06* | (2006.01) |
| *F16H 19/00* | (2006.01) |
| *F16H 19/02* | (2006.01) |

(52) U.S. Cl.
CPC .............. *A61B 34/71* (2016.02); *A61B 34/30* (2016.02); *B25J 18/06* (2013.01); *F16H 19/00* (2013.01); *F16H 19/02* (2013.01); *A61B 2034/301* (2016.02)

(58) Field of Classification Search
CPC .......... B25J 18/06; F16H 19/00; F16H 19/02; A61B 34/71; A61B 2034/301; A61B 34/30
See application file for complete search history.

(56) References Cited

U.S. PATENT DOCUMENTS

| | | |
|---|---|---|
| 2007/0078456 A1 | 4/2007 | Dumbauld et al. |
| 2007/0106297 A1 | 5/2007 | Dumbauld et al. |
| (Continued) | | |

FOREIGN PATENT DOCUMENTS

| | | |
|---|---|---|
| AU | 2007231795 A1 | 5/2008 |
| CA | 2 609 492 A1 | 5/2008 |
| (Continued) | | |

OTHER PUBLICATIONS

Japanese Office Action dated Jan. 14, 2020 in Japanese Patent Application No. 2018-553520.
(Continued)

*Primary Examiner* — Terence Boes
(74) *Attorney, Agent, or Firm* — Scully, Scott, Murphy & Presser, P.C.

(57) ABSTRACT

A bending mechanism includes: an elongated support member; a swivel that is supported at a distal end of the support member so as to swivel around an axis that intersects a longitudinal axis of the support member; a transmitter that are arranged along the longitudinal axis of the support member, transmits a driving force applied at a proximal end thereof, and makes the swivel swivel relative to the support member; and a regulator that regulates stress generated in the transmitter at each swivel position of the swivel with respect to the support member such that the stress does not exceed a prescribed threshold.

19 Claims, 13 Drawing Sheets

(56) References Cited

U.S. PATENT DOCUMENTS

| | | | |
|---|---|---|---|
| 2008/0195144 A1 | 8/2008 | Hashimoto | |
| 2010/0204697 A1 | 8/2010 | Dumbauld et al. | |
| 2011/0196419 A1* | 8/2011 | Cooper | A61B 18/1445 |
| | | | 606/206 |
| 2012/0123441 A1* | 5/2012 | Au | A61B 34/30 |
| | | | 606/130 |
| 2012/0221146 A1* | 8/2012 | Zhang | B25J 9/0078 |
| | | | 700/260 |
| 2013/0319143 A1* | 12/2013 | Huang | F16H 1/225 |
| | | | 74/89.14 |
| 2014/0194873 A1 | 7/2014 | Dumbauld et al. | |
| 2015/0141756 A1* | 5/2015 | Cheng | A61B 1/0016 |
| | | | 600/146 |
| 2016/0038239 A1* | 2/2016 | Yamanaka | A61B 34/37 |
| | | | 606/130 |
| 2016/0135914 A1 | 5/2016 | Isoda | |
| 2016/0310221 A1* | 10/2016 | Bar | A61B 34/20 |
| 2017/0080581 A1 | 3/2017 | Iida et al. | |
| 2019/0183592 A1* | 6/2019 | Shelton, IV | A61B 34/70 |

FOREIGN PATENT DOCUMENTS

| | | |
|---|---|---|
| EP | 1 913 879 A1 | 4/2008 |
| EP | 2 105 105 A1 | 9/2009 |
| EP | 3 025 669 A1 | 6/2016 |
| EP | 3159124 A1 | 4/2017 |
| JP | H06-008178 A | 1/1994 |
| JP | H06-262360 A | 9/1994 |
| JP | 2003-079638 A | 3/2003 |
| JP | 2007-044330 A | 2/2007 |
| JP | 4402313 B2 | 1/2010 |
| JP | 2012-125877 A | 7/2012 |
| JP | 2014-138879 A | 7/2014 |
| JP | 2015-023886 A | 2/2015 |
| JP | 2016-002414 A | 1/2016 |
| WO | 2011/059015 A1 | 5/2011 |
| WO | 2015/012023 A1 | 1/2015 |
| WO | WO 2015/194321 A1 | 12/2015 |
| WO | 2018/225212 A1 | 12/2018 |

OTHER PUBLICATIONS

International Search Report dated Aug. 29, 2017, received in International Application No. PCT/JP2017/021311, together with partial English Machine Translation.

International Search Report dated Feb. 7, 2017 issued in PCT/JP2016/085313.

* cited by examiner

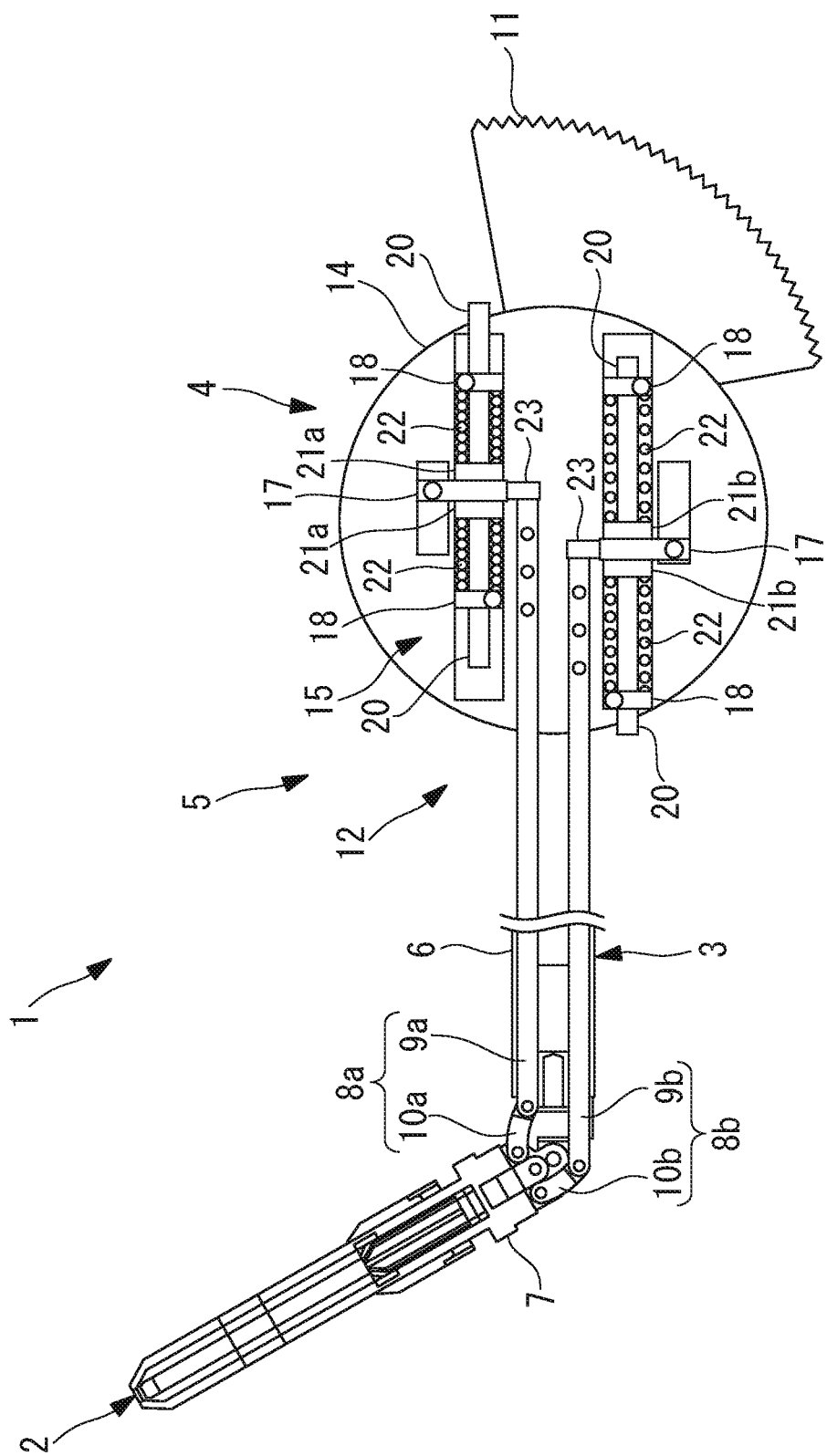

BENDING MECHANISM AND MEDICAL MANIPULATOR

CROSS-REFERENCE TO RELATED APPLICATIONS

This is a continuation of International Application PCT/JP2016/085313 which is hereby incorporated by reference herein in its entirety.

TECHNICAL FIELD

The present invention relates to a bending mechanism and a medical manipulator.

BACKGROUND ART

There is a known medical manipulator that is equipped, at the distal end of an elongated insertion part thereof, with a bending joint that is for changing the orientation of a treatment instrument provided at a distal end of the medical manipulator (for example, refer to PTL 1).

This medical manipulator is configured such that a swivel is made to swivel by pushing/pulling two links, which are arranged along the insertion part and are connected to the swivel, which is closer to the distal end than the bending joint, and the treatment instrument, which is fixed to the swivel, is thereby made to swivel.

CITATION LIST

Patent Literature

{PTL 1} The Publication of Japanese Patent No. 4402313

SUMMARY OF INVENTION

An aspect of the present invention provides a bending mechanism that includes: an elongated support member; a swivel supported at a distal end of the support member so as to swivel around an axis that intersects a longitudinal axis of the support member; a transmitter arranged along the longitudinal axis of the support member, transmitting a driving force applied at a proximal end thereof, and making the swivel swivel relative to the support member; and a regulator regulating stress generated in the transmitter at each swivel position of the swivel relative to the support member such that the stress does not exceed a prescribed threshold. The regulator includes an urging portion urging the transmitter at a position at a proximal end of the transmitter in a direction along the longitudinal axis to a reference position determined in accordance with a swivel angle of the swivel with respect to the support member.

Another aspect of the present invention provides a bending mechanism that includes: an elongated support member; a swivel supported at a distal end of the support member so as to swivel around an axis that intersects a longitudinal axis of the support member; a transmitter arranged along the longitudinal axis of the support member, transmitting a driving force applied at a proximal end thereof, and making the swivel swivel relative to the support member; a regulator regulating stress generated in the transmitter at each swivel position of the swivel relative to the support member such that the stress does not exceed a prescribed threshold; and an actuator supplying the driving force to the transmitter. The prescribed threshold is set to a different value depending on a swivel angle of the swivel with respect to the support member, and the regulator controls the driving force generated by the actuator in accordance with the swivel angle.

BRIEF DESCRIPTION OF DRAWINGS

FIG. 8B is a rear view illustrating the operation part in FIG. 8A.

DESCRIPTION OF EMBODIMENTS

Figure 1:
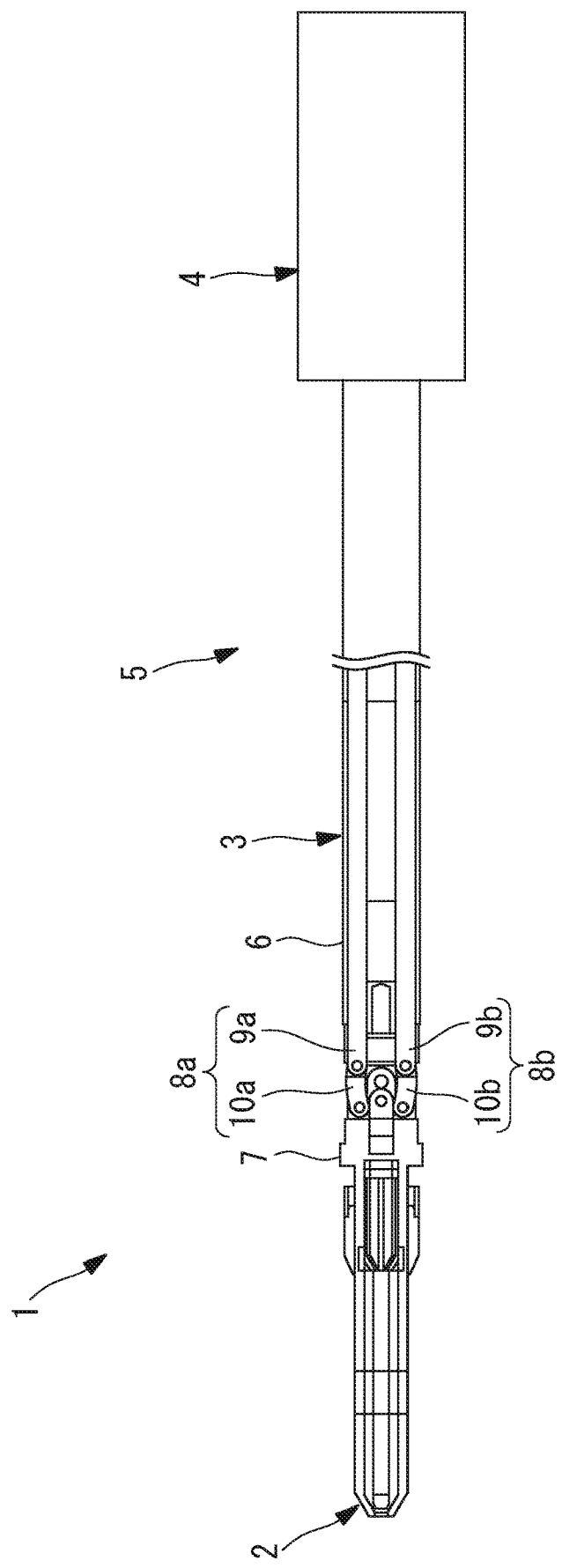
FIG. 1 is an overall configuration diagram illustrating a medical manipulator according to an embodiment of the present invention.

Hereafter, a bending mechanism 5 and a medical manipulator 1 according to an embodiment of the present invention will be described while referring to the drawings.

As illustrated in FIG. 1, the medical manipulator 1 according to this embodiment includes a treatment instrument 2 that is for treating an affected part, an elongated insertion part 3, and an operation part 4 that is connected to a proximal end of the insertion part 3. The bending mechanism 5 is constituted by the insertion part 3 and the operation part 4. The treatment instrument 2 is attached to a swivel 7 of the insertion part 3, which is described later.

As illustrated in FIG. 1, the insertion part 3 includes: an elongated support member 6; the swivel 7 that is supported at a distal end of the support member 6 so as to be able to swivel around a swiveling axis that is perpendicular to a longitudinal axis of the support member 6; and two sets of links (driving-force transmitting member) 8a and 8b that transmit a driving force applied at the operation part 4 at the proximal end of the support member 6 and make the swivel 7 swivel relative to the support member 6. The sets of links 8a and 8b respectively include: long first links 9a and 9b that are arranged along the longitudinal axis of the support member 6; and short second links 10a and 10b that are connected to the first links 9a and 9b and the swivel 7 so as to be able to swivel around an axis that is parallel to the swiveling axis.

Figure 2:
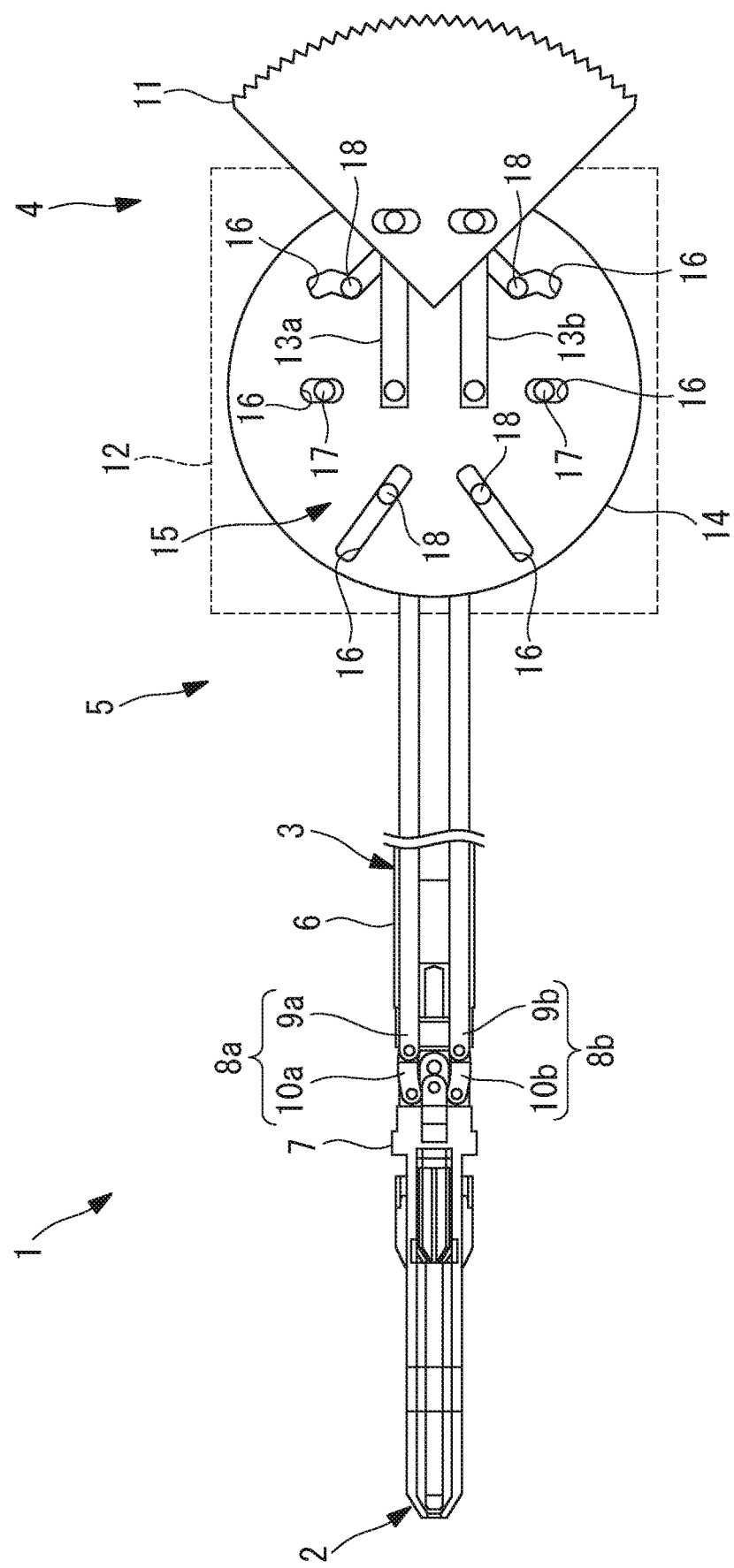
FIG. 2 is a plan view illustrating an operation part of the medical manipulator in FIG. 1.
Figure 3:
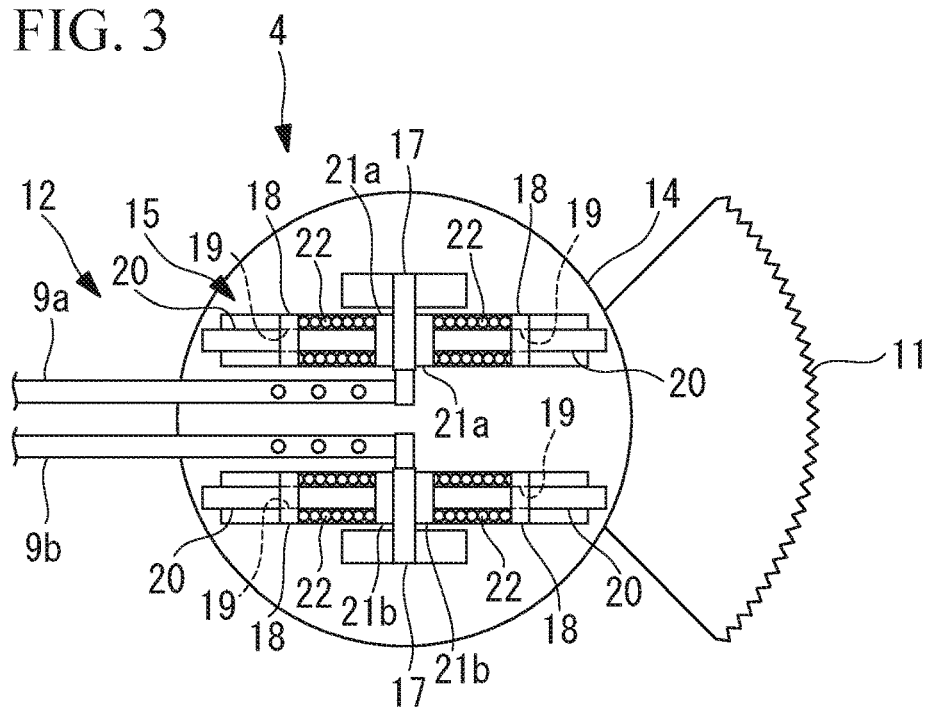
FIG. 3 is a rear view illustrating the operation part in FIG. 2.

As illustrated in FIGS. 2 and 3, the operation part 4 includes a handle 11 which is operated by an operator and to which a driving force is applied, and a driving-force converting unit (actuator) 12 that supplied the driving force applied to the handle 11 to the two sets of links 8a and 8b.

The handle 11 is formed in a fan shape and the outer peripheral surface thereof is given a jagged shape. The handle 11 can be swung by touching the outer peripheral surface with a finger and moving the finger in a peripheral direction.

The driving-force converting unit 12 includes: links 13a and 13b, each of which have one end connected to the handle 11; a cam plate (cam mechanism) 14 that is connected to the other ends of the links 13a and 13b and is provided so as to be able to be rotate in response to a force received from the links 13a and 13b; and a floating mechanism (stress regulating part) 15 that is attached to the cam plate 14.

The cam plate 14 includes a plurality of cam grooves 16. Stoppers 17 and support blocks 18, which are described later, are movably fitted in the cam grooves 16. The cam grooves 16 are shaped so as to be able to guide movement of the stoppers 17 and the support blocks 18 to appropriate positions in accordance with the rotation angle of the cam plate 14. Specifically, the distances between the stoppers 17 and the support blocks 18 are appropriately set in accordance with the rotation angle of the cam plate 14.

As illustrated in FIGS. 4A to 4D, the floating mechanism 15 includes: flat-plate-shaped stoppers 17 that are fitted into the cam grooves 16 formed in the cam plate 14 so as to be able to move along the cam grooves 16; flat-plate-shaped support blocks 18 that are arranged such that the stoppers 17 are interposed therebetween with spaces on both sides of the stoppers 17 and that are fitted into the cam grooves 16 formed in the cam plate 14 so as to able move along the cam grooves 16; shafts 20 that are movably inserted into through holes 19 formed so as to penetrate through the support blocks 18 in a plate thickness direction; and compression coil springs (elastic member, urging member) 22 that are arranged between pressing plates (pressing member) 21a and 21b, which are provided at distal ends of the shafts 20, and the support blocks 18.

The compression coil springs 22 urge the pressing plates 21a and 21b of the shafts 20 in directions so as to move the pressing plates 21a and 21b away from the support blocks 18 and cause the pressing plates 21a and 21b to closely contact the surfaces of the stoppers 17 with an urging force determined by the distances between the support blocks 18 and the stoppers 17 such that the two surfaces of each stopper 17 are sandwiched between two pressing plates 21a and 21b.

Flange portions 23, which have substantially the same thickness as the stoppers 17, are fixed to the proximal ends of the first links 9a and 9b. The flange portions 23 are arranged adjacent to the stoppers 17 and are each interposed in a plate thickness direction between the corresponding stopper 17 and two pressing plates 21a or 21b.

Figure 4A:
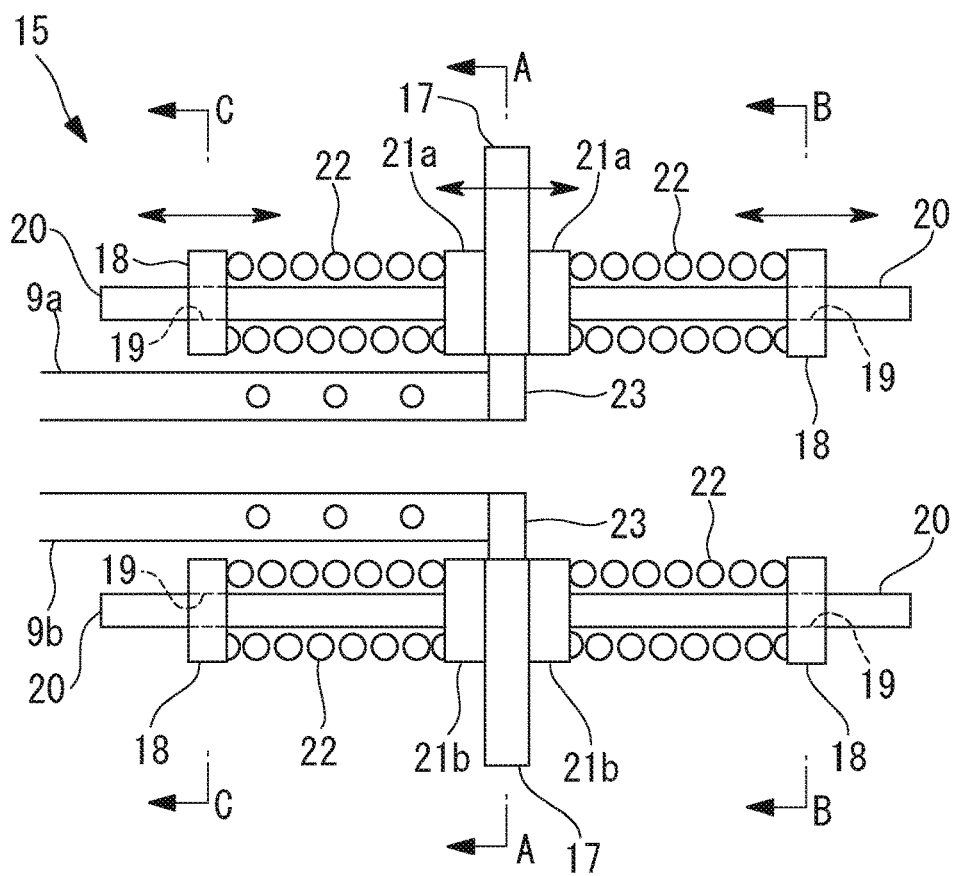
FIG. 4A is a plan view illustrating a floating mechanism provided in the operation part in FIG. 2.
Figure 4B:
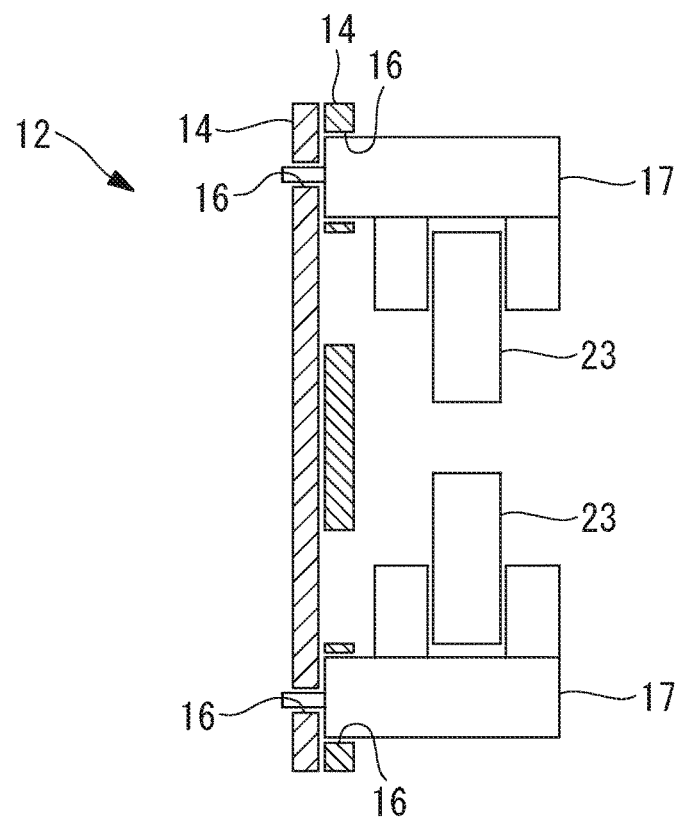
FIG. 4B is a diagram illustrating a cross section of the floating mechanism in FIG. 4A taken along line A-A and looking in the direction of the arrows.
Figure 4C:
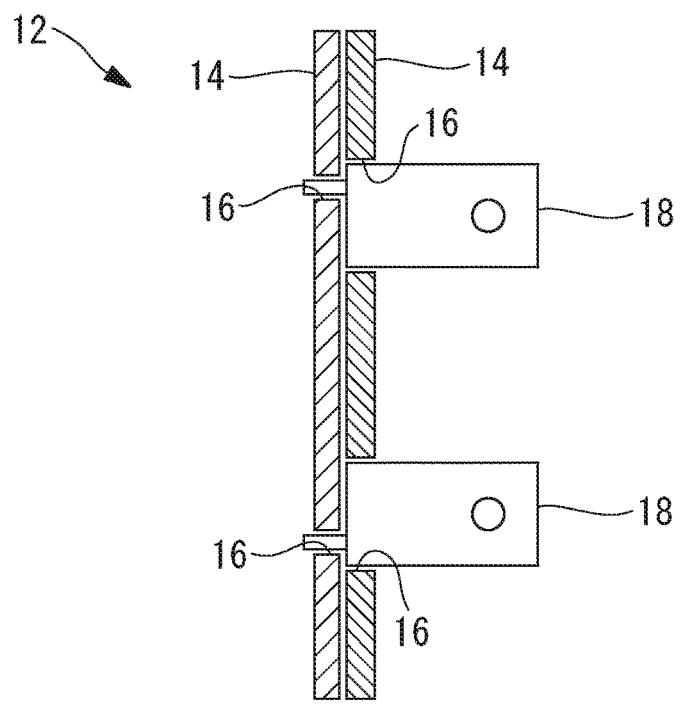
FIG. 4C is a diagram illustrating a cross section of the floating mechanism in FIG. 4A taken along line B-B and looking in the direction of the arrows.
Figure 4D:
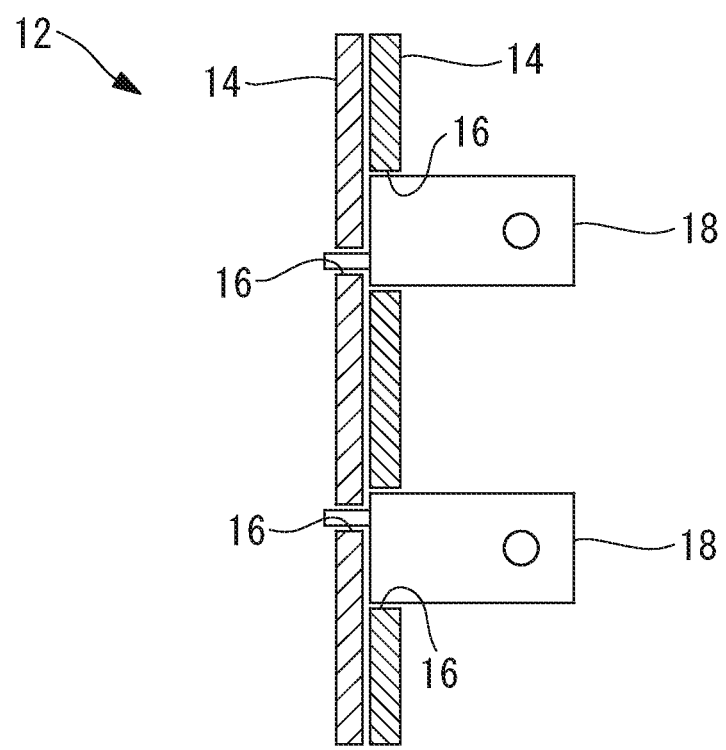
FIG. 4D is a diagram illustrating a cross section of the floating mechanism in FIG. 4A taken along the line C-C and looking in the direction of the arrows.
Figure 5:
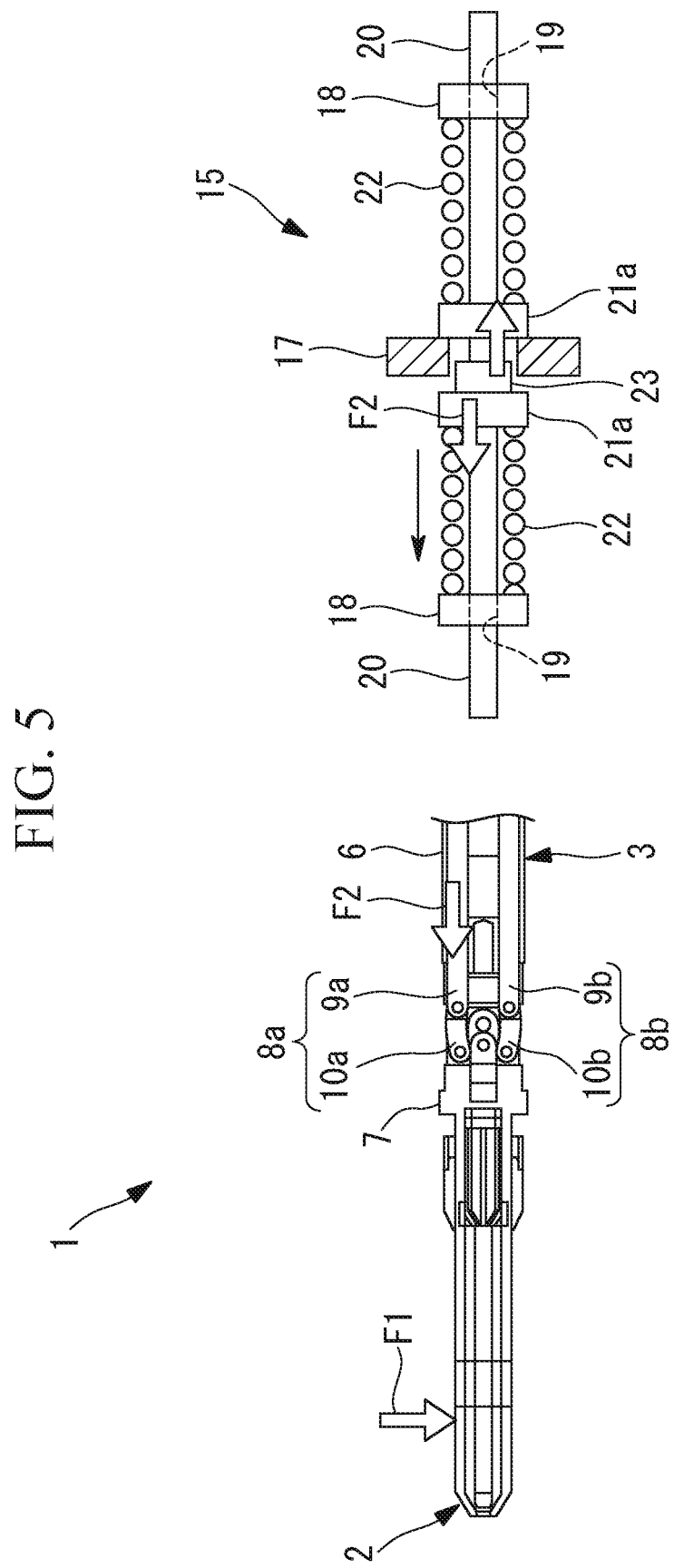
FIG. 5 is a diagram for explaining operation of the floating mechanism in FIG. 4A.

The shafts 20 are arranged substantially parallel to the longitudinal axes of the first links 9a and 9b. Thus, in a state where a force less than or equal to the urging forces of the compression coil springs 22 acts on the first links 9a and 9b in the longitudinal axis direction, as illustrated in FIG. 4A, the flange portion 23 of each shaft 20 is maintained unchanged at a position adjacent to the stopper 17 in the state of being sandwiched between the two pressing plates 21a and 21b. On the other hand, when a force F2 that exceeds the urging force of either of the compression coil springs 22 acts on the first link 9a or 9b in the longitudinal axis direction due to application of an external force F1, as illustrated in FIG. 5, one compression coil spring 22 is compressed and the corresponding flange portion 23 moves away from the other pressing plate 21a or 21b, and as a result the flange portion 23 is moved to a different position from the stopper 17 in the longitudinal axis direction.

In addition, when the handle 11 is operated and rotation of the handle 11 is converting into rotation of the cam plate 14 by the links 13a and 13b, the cam grooves 16 provided in the cam plate 14 move, and as a result, the support blocks 18 and the stoppers 17, which are engaged with the cam grooves 16, move along the cam grooves 16. The stoppers 17 are guided to reference positions by the cam grooves 16 such that the flange portions 23 at the proximal ends of the first links 9a and 9b come to be arranged at reference positions determined by the rotation angle of the handle 11.

On the other hand, the cam grooves 16 for the support blocks 18 are formed so as to be disposed at positions such that the distance between the support blocks 18 and the stoppers 17 changes in accordance with the rotation angle (swivel angle) of the handle 11.

Figure 6:
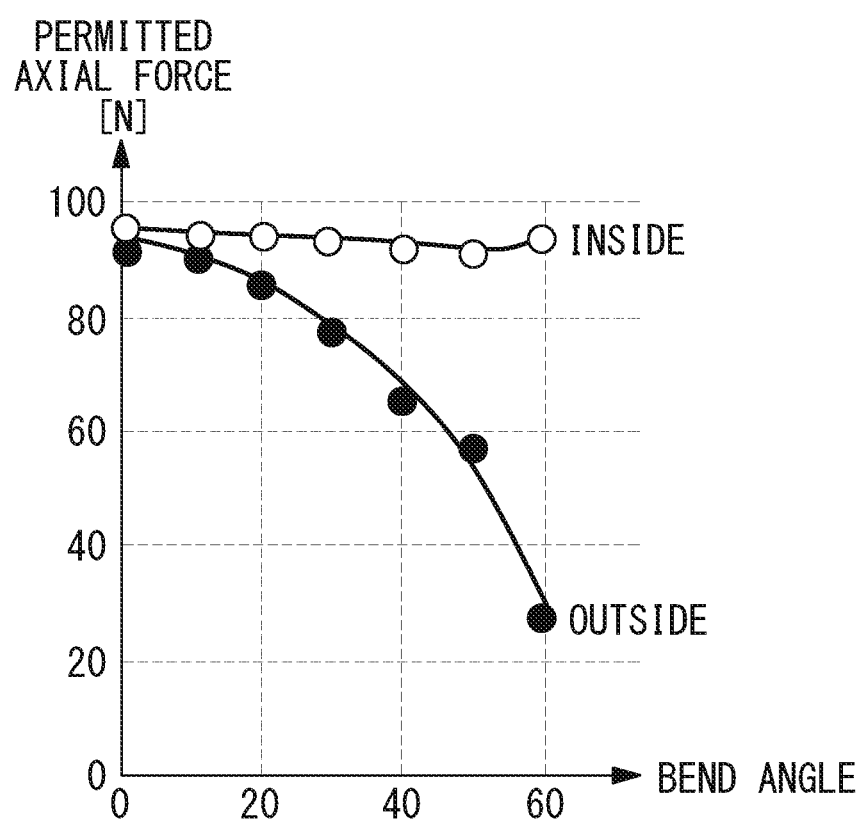
FIG. 6 is a graph illustrating the relationships between the bend angle of an inner first link in FIG. 5 and the bend angle of an outer first link in FIG. 5 and a permitted axial force.

For example, in the case of the thus-configured bending mechanism 5, in the first link 9a on the inside of the bend and the first link 9b on the outside of the bend of the bending joint, as illustrated in FIG. 6, the permitted axial force of the first link 9b on the outside of the bend is greatly reduced as the bend angle increases, whereas the permitted axial force of the first link 9a on the inside of the bend of the bending joint tends to be only slightly reduced.

Figure 7:
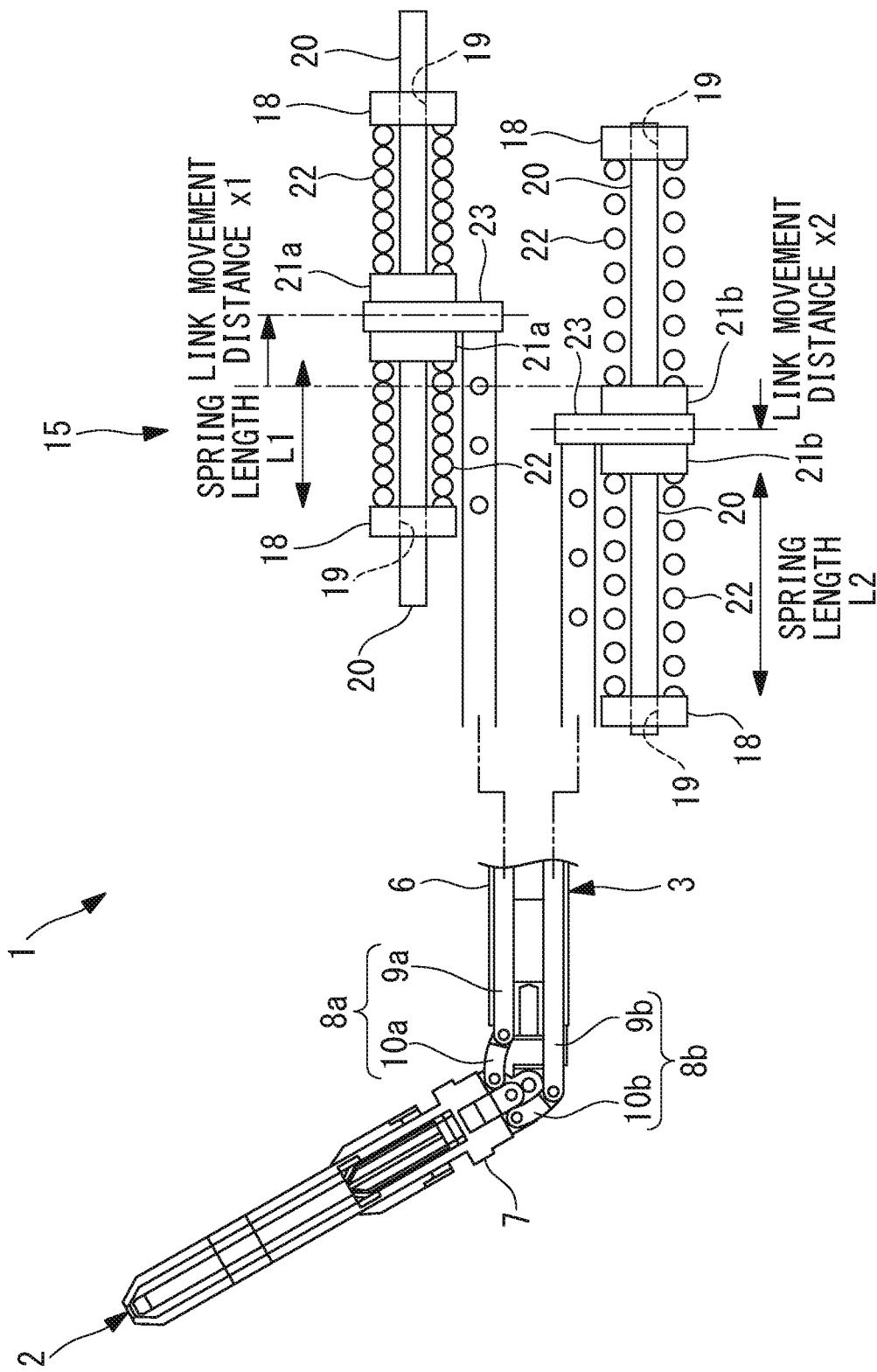
FIG. 7 is a plan view for explaining operation of the floating mechanism in FIG. 4A.

Therefore, in this embodiment, the cam grooves 16 of the cam plate 14 are shaped so as to cause the stoppers 17 and the support blocks 18 to move when the cam plate 14 is rotated such that the interval between the stopper 17 and the support block 18 on the outside of the bend is greatly increased and such that the interval between the stopper 17 and the support block 18 on the inside of the bend is slightly increased, as illustrated in FIG. 7.

As a result, when the interval between a stopper 17 and a support block 18 increases, the compression coil spring 22 interposed therebetween is stretched, and therefore the rigidity of the compression coil spring 22 is reduced, the first link 9a or 9b is compressed by a smaller axial force acting thereon, and the flange portion 23, i.e., the proximal end of the first link 9a or 9b can be made to move in either direction along the longitudinal axis from a reference position stipulated by the stopper 17.

Hereafter, operation of the thus-configured bending mechanism 5 and medical manipulator 1 according to this embodiment will be described.

When an affected part is to be treated using the medical manipulator 1 according to this embodiment, the treatment instrument 2 at the distal end of the insertion part 3 is arranged in the vicinity of the affected part by inserting the insertion part 3 into the inside of the patient's body, the handle 11 provided in the operation part 4 is operated and the swivel 7 is made to swivel relative to the support member 6, and in this way, the posture of the treatment instrument 2 with respect to the affected part is adjusted.

Figure 8A:
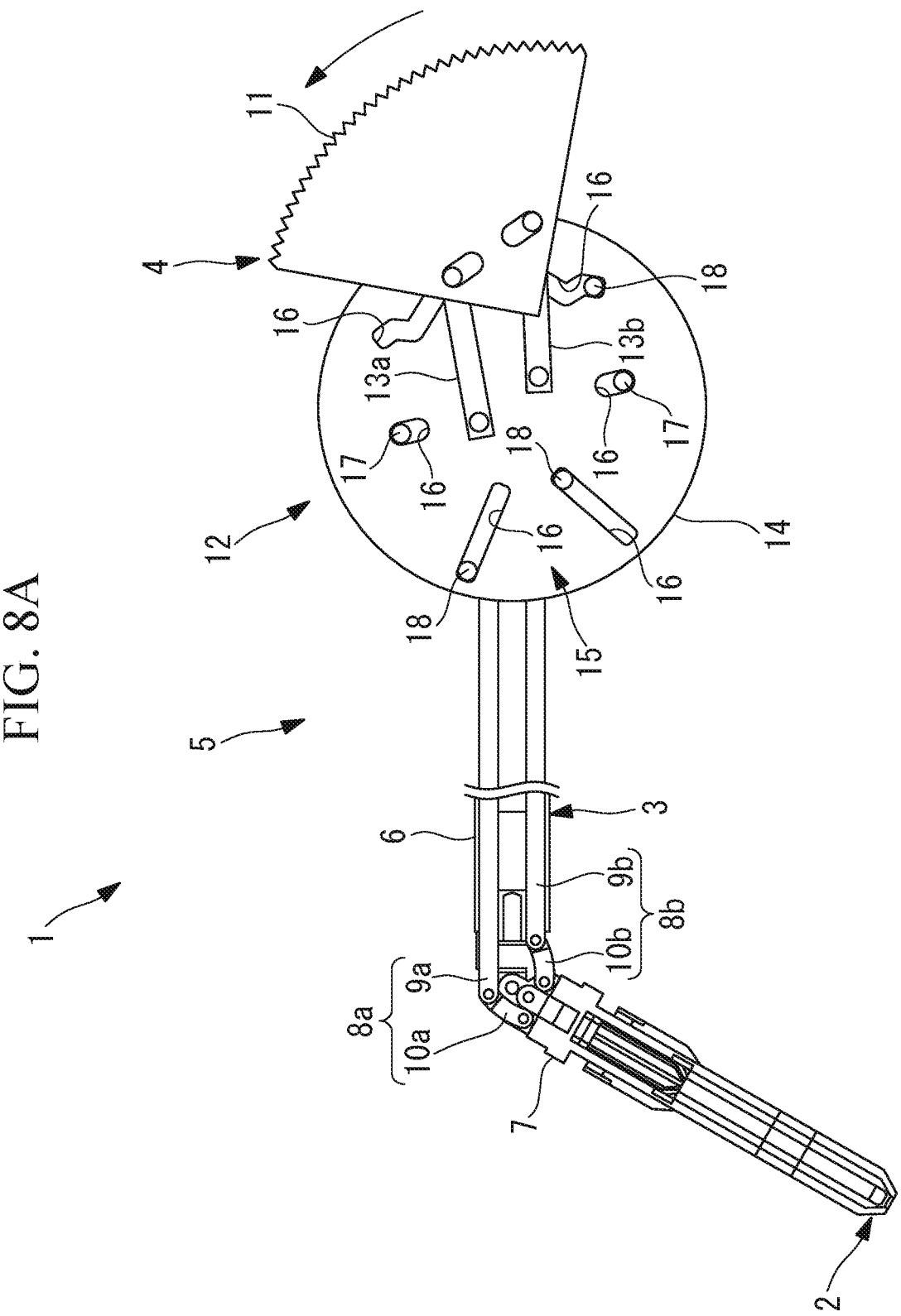
FIG. 8A is a plan view for explaining operation of the operation part in FIG. 2.

When the handle 11 is operated using a finger so as to rotate the handle 11 in one direction, as illustrated in FIGS. 8A and 8B, a rotational force is transmitted to the cam plate 14 by the two links 13a and 13b connected to the handle 11 and the cam plate 14 is made to rotate to an angle in accordance with the rotation of the handle 11. Two stoppers 17 and four support blocks 18 are fitted into the cam grooves 16 provided in the cam plate 14, and therefore the stoppers 17 and the support blocks 18 are made to move along the cam grooves 16, which are moved by the rotation of the cam plate 14.

As described above, the shapes of the cam grooves 16 are formed such that the stoppers 17 and the support blocks 18 are arranged at appropriate positions in accordance with a swivel angle of the swivel 7 corresponding to the rotation angle of the cam plate 14, and therefore the intervals between the stoppers 17 and the support blocks 18 are appropriately set in accordance with the swivel angle of the swivel 7.

In other words, when the swivel 7 swivels with respect to the support member 6, as illustrated in FIG. 7, the distance between the stopper 17 and the support block 18 on the side of the first link 9*b*, which is arranged on the outside of the bend, considerably increases, whereas the distance between the stopper 17 and the support block 18 on the side of the first link 9*a*, which is arranged on the inside of the bend, slightly increases. Thus, compression of the compression coil spring 22 on the outside of the bend is considerably relaxed and the urging force is considerably reduced, whereas compression of the compression coil spring 22 on the inside of the bend is slightly relaxed and the urging force is slightly reduced.

Therefore, when an external force acts on the distal end of the treatment instrument 2, which is fixed to the swivel 7, the compression coil spring 22 on the outside of the bend is compressed by a smaller external force than the compression coil spring 22 on the inside of the bend, and the movement, in the longitudinal axis direction, of the flange portion 23 fixed to the proximal end of the first link 9*b* is permitted. The permitted axial force of the first link 9*b* on the outside of the bend is considerably reduced and movement at the proximal end side of the first link 9*b* is permitted with just a small external force, and therefore there is an advantage in that a situation in which an excessive axial force exceeding the permitted axial force acts on the first link 9*b* can be avoided.

In this case, the permitted axial force of the first link 9*a* on the inside of the bend is not greatly reduced, and therefore a state in which the proximal end of the first link 9*a* is not moved by a small external force is maintained. As a result, the first link 9*b* on the outside of the bend, where the permitted axial force is reduced, can be prevented from being damaged, and the external force is accommodated by the first link 9*a* on the inside of the bend where the permitted axial force has not been considerably reduced.

When the axial force acting on the first link 9*a* on the inside of the bend reaches the permitted axial force, for the inside first link 9*a*, the compression coil spring 22 is compressed and the flange portion 23 at the proximal end is made to move as well, and a situation in which an excessive axial force exceeding the permitted axial force acts on the first link 9*a* can be avoided. Thus, there is no need to increase the cross section of the first link 9*a* in consideration of the reduction in the permitted axial force, and there is an advantage in that the insertion part 3 can be made narrow while preventing the occurrence of damage.

Figure 9:
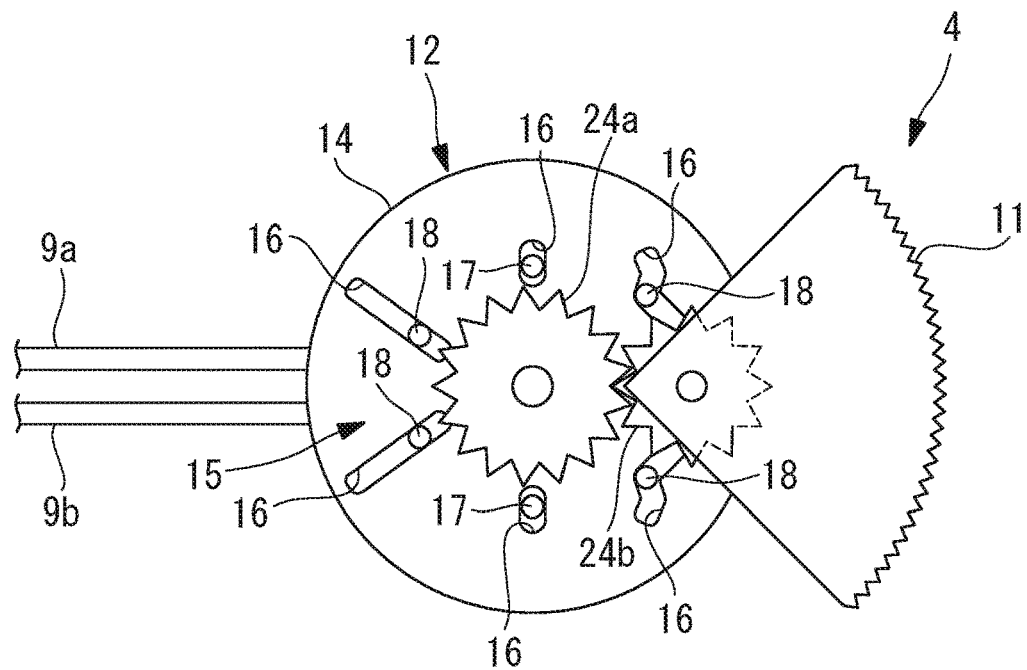
FIG. 9 is a plan view illustrating a first modification of the operation part in FIG. 2.

In addition, although the rotation of the handle 11 is transmitted to the cam plate 14 by the links 13*a* and 13*b* in this embodiment, the rotation of the handle 11 may be alternatively transmitted by gears 24*a* and 24*b*, as illustrated in FIG. 9. In this case, the axes of the gears 24*a* and 24*b* are connected to each other such that the inter-axis distance therebetween is maintained by a connection member, which is not illustrated, and it is sufficient that the gears 24*a* and 24*b* and the cam plate 14 be connected to each other by an Oldham coupling or the like (not illustrated) that transmits rotation therebetween while allowing eccentricity.

Furthermore, the compression coil springs 22 have been exemplified as the urging means, but cylinders that generate an urging force through the pressure of a fluid such as air or a liquid may instead be adopted. In addition, magnets that generate an urging force through magnetism may be adopted.

Figure 10:
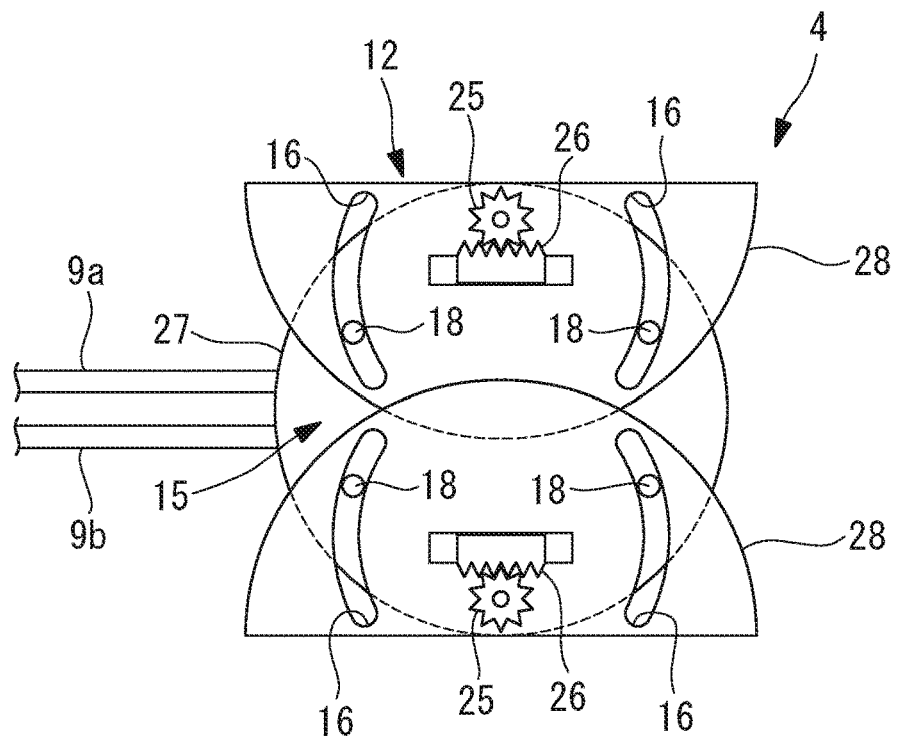
FIG. 10 is a plan view illustrating a second modification of the operation part in FIG. 2.

Furthermore, as illustrated in FIG. 10, a motor (not illustrated) that makes stoppers 17 move via pinion gears 25 and rack gears 26 may be adopted instead of the handle 11 and cam plates 27 and 28 that are made to rotate together with movement of the stoppers 17 may be adopted. It is sufficient that the motor be a motor that is made to operate on the basis of an operation command signal input by an operator.

Figure 11:
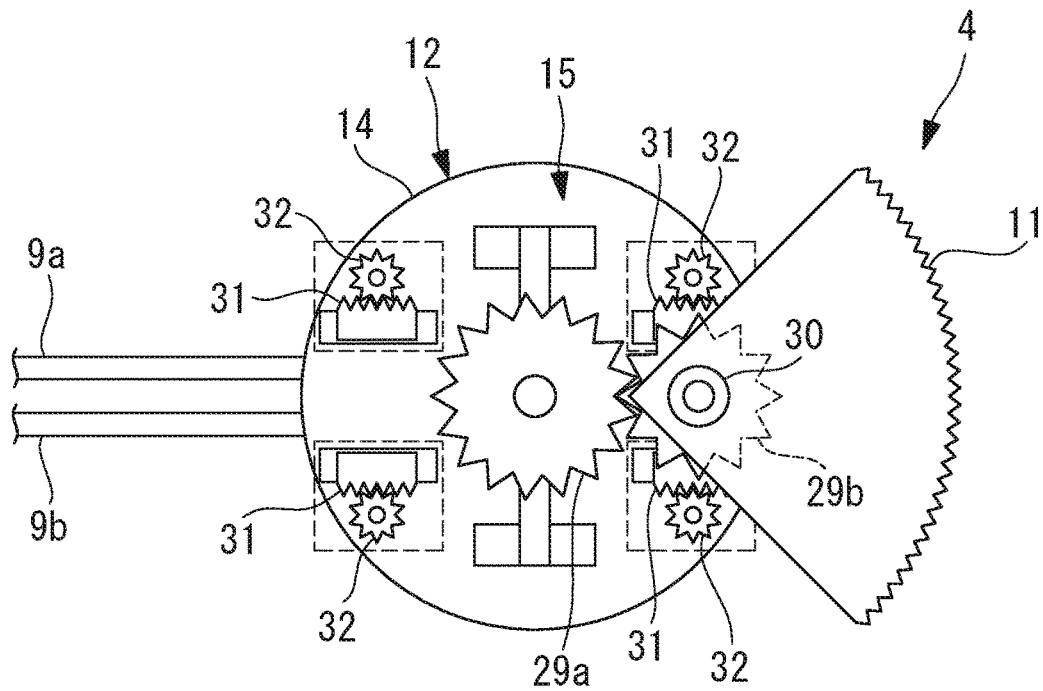
FIG. 11 is a plan view illustrating a third modification of the operation part in FIG. 2.

Furthermore, as illustrated in FIG. 11, a configuration may be adopted in which the rotation of the handle 11 is converted into movement of the stoppers 17 by the gears 29*a* and 29*b*, the rotation angle of the handle 11 is detected by an encoder 30, and a motor (not illustrated) and a rack gear 31 and a pinion gear 32 are used to make each support block 18 move on the basis of the detected rotation angle.

In addition, rather than detect the rotation angle of the handle 11 using the encoder 30, the movement amounts of the first links 9*a* and 9*b* may be detected or the swivel angle of the swivel 7 may be detected.

Figure 12:
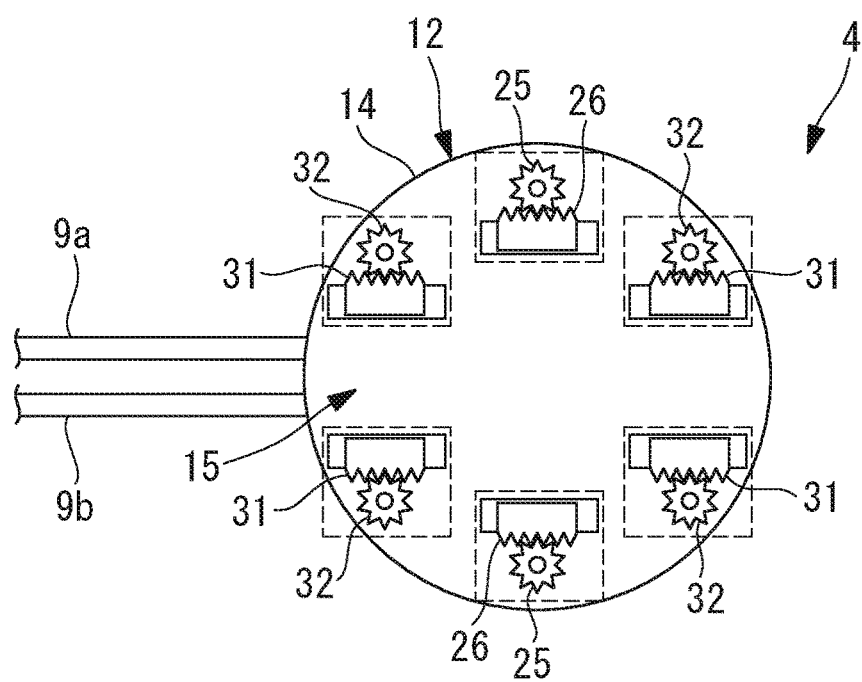
FIG. 12 is a plan view illustrating a fourth modification of the operation part in FIG. 2.

Furthermore, as illustrated in FIG. 12, the stoppers 17 and the support blocks 18 may be made to move by a motor (not illustrated), rack gears 26 and 31, and pinion gears 25 and 32. In this case, it is sufficient to operate a motor that drives the stoppers 17 and a motor that drives the support blocks 18 on the basis of operation command signals input from the operator.

Alternatively, a configuration may be adopted in which the rotation amount of a motor that drives the stoppers 17 is detected by an encoder (not illustrated) and a motor that drives the support blocks 18 is operated on the basis of the detected rotation amount. In this case, the movement amounts of the first links 9*a* and 9*b* may be detected or the swivel angle of the swivel 7 may be detected rather than detecting the rotation amount of the motor using an encoder.

Figure 13:
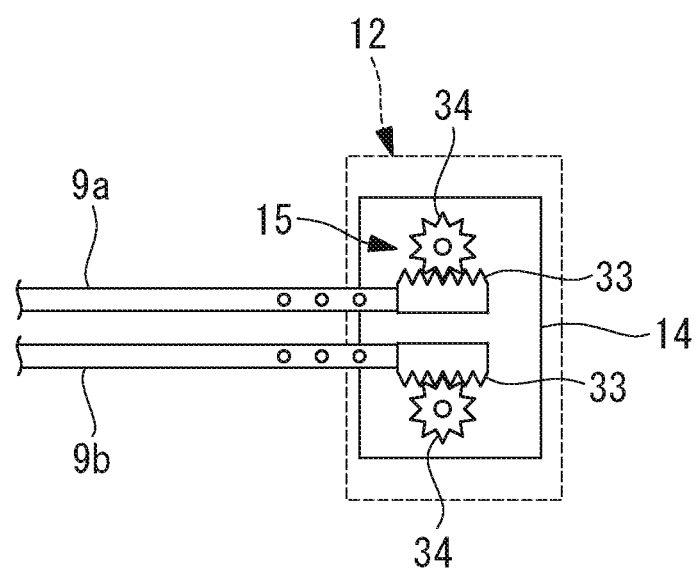
FIG. 13 is a plan view illustrating a fifth modification of the operation part in FIG. 2.

Although it has been assumed that the urging force of urging means such as the compression coil springs 22 is regulated in accordance with the swivel angle of the swivel 7 with respect to the support member 6 in the above-described embodiments, alternatively, as illustrated in FIG. 13, a configuration may be adopted in which pinion gears 34 that are meshed with rack gears 33, which are fixed to the proximal ends of the first links 9*a* and 9*b*, are made to rotate by a motor (not illustrated) and the torque generated by the motor is changed into an appropriate value in accordance with the swivel angle of the swivel 7 with respect to the support member 6.

In this case as well, the rotation amount of a motor may be detected by an encoder (not illustrated) and the torque generated by the motor may be changed in accordance with the rotation amount of the motor detected by the encoder. In addition, the movement amount of the first links 9*a* and 9*b* may be detected or the swivel angle of the swivel 7 may be detected rather than detecting the rotation amount of the motor using an encoder.

Furthermore, although the links 8*a* and 8*b* have been exemplified as driving-force transmitting members in this embodiment, torque shafts or wires may be used instead.

In addition, a configuration has been described in which a force acting on the first links 9*a* and 9*b* does not exceed a permitted axial force, but alternatively, stress generated in the links 8*a* and 8*b* when any other part becomes damaged may serve as a threshold.

The above-described embodiment also leads to the following invention.

An aspect of the present invention provides a bending mechanism that includes: an elongated support member; a swivel that is supported at a distal end of the support member so as to be able to swivel around an axis that intersects a longitudinal axis of the support member; a driving-force transmitting member that is arranged along the longitudinal axis of the support member, transmits a driving force applied at a proximal end thereof, and makes the swivel swivel relative to the support member; and a stress regulating part that regulates stress generated in the driving-force transmitting member at each swivel position of the swivel relative to the support member such that the stress does not exceed a prescribed threshold.

According to this aspect, when a driving force is applied to the driving-force transmitting member at the proximal end of the support member, the driving force, which is transmitted by the driving-force transmitting member, is transmitted to the swivel and the swivel is made to swivel around an axis at the distal end of the support member. In this case, stress generated in the driving-force transmitting member is regulated at each swivel position of the swivel with respect to the support member through operation of the stress regulating part such that the stress does not exceed a prescribed threshold. Consequently, even when the rigidity of the swivel varies depending on the swivel angle, excessive stress acting on each part can be avoided. In this case, the rigidity of various parts including the driving-force transmitting member are improved and consequently an increase in stress does not occur, and since the stress itself is regulated, it is possible to prevent an increase in the sectional dimensions of each part and make the insertion part narrow.

In the above-described aspect, when stress generated in the driving-force transmitting member reaches the prescribed threshold, the stress regulating part may permit movement of the driving-force transmitting member in a direction that results in the stress being reduced.

With this configuration, when stress equal to a prescribed threshold is generated in the driving-force transmitting member, the driving-force transmitting member is allowed to move by the stress regulating part in a direction that results in the stress being reduced and a situation in which an excessive stress that exceeds the prescribed threshold acts is avoided.

Furthermore, in the above-described aspect, the prescribed threshold may be set to a different value depending on a swivel angle of the swivel with respect to the support member.

With this configuration, a situation in which an excessive stress acts on each part can be avoided by setting a higher threshold for a swivel angle where the rigidity is high and a lower threshold for a swivel angle where the rigidity is low in accordance with a rigidity that varies depending on the swivel angle of the swivel.

In addition, in the above-described aspect, the driving-force transmitting member may be capable of transmitting the driving force in both directions along the longitudinal axis of the support member.

With this configuration, generation of excessive stress can be prevented in both directions when the driving force is transmitted in both directions along the longitudinal axis of the support member.

Furthermore, in the above-described aspect, the stress regulating part may include an urging means that urges the driving-force transmitting member at a position at a proximal end of the driving-force transmitting member in a direction along the longitudinal axis to a reference position determined in accordance with a swivel angle of the swivel with respect to the support member.

With this configuration, when the proximal end of the driving-force transmitting member is operated and a driving force acts in the longitudinal axis direction, the proximal end of the driving-force transmitting member is maintained at the reference position by the urging means in the case where the driving force is lower than a prescribed threshold, and therefore the swivel is made to swivel at a swivel angle corresponding to a movement amount of the reference position. On the other hand, in the case where the driving force reaches the prescribed threshold, the proximal end of the driving-force transmitting member is made to move from the reference position against the urging force and a situation in which an excessive stress that exceeds the prescribed threshold acts is avoided.

Furthermore, in the above-described aspect, the stress regulating part may include: a flat-plate-shaped flange portion that is fixed to a proximal end of the driving-force transmitting member; a flat-plate-shaped stopper that has an identical plate thickness to the flange portion, that is arranged next to the flange portion in a direction perpendicular to the longitudinal axis, and is arranged at the reference position in accordance with the swivel angle; and a pair of pressing members that are arranged at positions such that the stopper and the flange portion are simultaneously interposed therebetween in the plate thickness direction. The urging means may urge the pressing members in directions such that the pressing members closely contact the stopper.

With this configuration, in the case where the stress generated in the driving-force transmitting member is lower than the prescribed threshold, when a driving force is applied and the driving-force transmitting member is made to move, the swivel is made to swivel relative to the support member by the driving force transmitted by the driving-force transmitting member and the stopper is arranged at a reference position in accordance with the swivel angle. At this time, the pressing members are made to closely contact the stopper by the urging force of the urging means and the stopper and the flange portion are maintained at the same position in the longitudinal axis direction.

On the other hand, in the case where the stress generated in the driving-force transmitting member exceeds the urging force of the urging means and reaches the prescribed threshold, the flange portion at the proximal end of the driving-force transmitting member is made to move against the urging force and as a result the stress is reduced. Consequently, a situation in which an excessive stress that exceeds the prescribed threshold acts on each part is avoided.

Furthermore, in the above-described aspect, the urging means may be an elastic member.

With this configuration, in the case where stress generated in the driving-force transmitting member reaches the prescribed threshold, the elastic member is made to elastically deform and as a result an increase in stress and a situation in which an excessive stress acts on each part can be avoided.

In addition, in the above-described aspect, the urging means may be a cylinder that generates an urging force using a fluid.

With this configuration, in the case where the stress generated in the driving-force transmitting member reaches the prescribed threshold, the driving-force transmitting member is made to move against the urging force generated by the pressure of the cylinder and as a result an increase in stress and a situation in which an excessive stress acts on each part can be avoided.

In addition, in the above-described aspect, the urging means may be a magnet that generates an urging force through magnetism.

With this configuration, in the case where stress generated in the driving-force transmitting member reaches the prescribed threshold, the driving-force transmitting member is made to move against the urging force generated through the magnetism of the magnet and as a result an increase in stress and a situation in which an excessive stress acts on each part can be avoided.

Furthermore, in the above-described aspect, the bending mechanism may further include: a support block that is arranged at a position such that the urging means is interposed between the support block and the stopper and that supports an urging force; and a cam mechanism that changes a distance between the support block and the stopper in accordance with the swivel angle.

With this configuration, the distance between the support block and the stopper is changed by the cam mechanism in accordance with the swivel angle of the swivel with respect to the support member and an appropriate urging force in accordance with the rigidity that changes depending on the swivel angle is generated by the urging means, and as a result a situation in which an excessive stress acts on each part can be avoided at each swivel position.

Furthermore, in the above-described aspect, the bending mechanism may further include: a support block that is arranged at a position such that the urging means is interposed between the support block and the stopper and that supports an urging force; and an actuator that changes a distance between the support block and the stopper in accordance with the swivel angle.

With this configuration, the distance between the support block and the stopper is changed by the actuator in accordance with the swivel angle of the swivel with respect to the support member and an appropriate urging force in accordance with the rigidity that changes depending on the swivel angle is generated by the urging means, and as a result a situation in which an excessive stress acts on each part can be avoided at each swivel position.

Furthermore, in the above-described aspect, the bending mechanism may further include an actuator that supplies the driving force to the driving-force transmitting member, and the stress regulating part may control the driving force generated by the actuator in accordance with the swivel angle.

With this configuration, an appropriate driving force is generated in accordance with the rigidity, which changes depending on the swivel angle, by controlling the driving force generated by the actuator that supplies the driving force to the driving-force transmitting member, and as a result a situation in which an excessive stress acts on each part can be avoided at each swivel position.

In addition, another aspect of the present invention provides a medical manipulator that includes any one of the bending mechanisms described above; and a treatment instrument that is attached to the swivel.

REFERENCE SIGNS LIST 1 medical manipulator
2 treatment instrument
5 bending mechanism
6 support member
7 swivel
8a, 8b link (driving-force transmitting member)
12 driving-force converting unit (actuator)
14, 27, 28 cam plate (cam mechanism)
15 floating mechanism (stress regulating part)
17 stopper
18 support block
21a, 21b pressing plate (pressing member)
22 compression coil spring (elastic member, urging means)
23 flange portion

The invention claimed is:

1. A bending mechanism comprising:
an elongated support member;
a swivel supported at a distal end of the support member so as to swivel around an axis that intersects a longitudinal axis of the support member;
a transmitter arranged along the longitudinal axis of the support member, transmitting a driving force applied at a proximal end thereof, and making the swivel swivel relative to the support member; and
a regulator regulating stress generated in the transmitter at each swivel position of the swivel relative to the support member such that the stress does not exceed a prescribed threshold,
wherein the regulator includes an urging portion urging the transmitter at a position at a proximal end of the transmitter in a direction along the longitudinal axis to a reference position determined in accordance with a swivel angle of the swivel with respect to the support member, and
wherein the transmitter comprises one or more links configured to transmit the driving force in a distal direction and in a proximal direction along the longitudinal axis of the support member.

2. The bending mechanism according to claim 1, wherein when stress generated in the transmitter reaches the prescribed threshold, the regulator permits movement of the transmitter in a direction that results in the stress being reduced.

3. The bending mechanism according to claim 1, wherein the prescribed threshold is set to a different value depending on a swivel angle of the swivel with respect to the support member.

4. The bending mechanism according to claim 1, wherein the regulator includes:
a flat-plate-shaped flange fixed to a proximal end of the transmitter;
a flat-plate-shaped stopper having an identical plate thickness to the flange, being arranged next to the flange in a direction perpendicular to the longitudinal axis, and being arranged at the reference position in accordance with the swivel angle; and
a pair of pressing members arranged at positions such that the stopper and the flange are simultaneously interposed therebetween in the plate thickness direction, and wherein the urging portion of the regulator urges the pressing members in directions such that the pressing members closely contact the stopper.

5. The bending mechanism according to claim 4, wherein the urging portion of the regulator is an elastic body.

6. The bending mechanism according to claim 4, wherein the urging portion of the regulator is a cylinder that generates an urging force using a fluid.

7. The bending mechanism according to claim 4, wherein the urging portion of the regulator is a magnet that generates an urging force through magnetism.

8. The bending mechanism according to claim 4, further comprising:
a support block arranged at a position such that the urging portion is interposed between the support block and the stopper and supporting an urging force; and
a cam plate changing a distance between the support block and the stopper in accordance with the swivel angle.

9. The bending mechanism according to claim 4, further comprising:
a support block arranged at a position such that the urging portion is interposed between the support block and the stopper and supporting an urging force; and
an actuator changing a distance between the support block and the stopper in accordance with the swivel angle.

10. A bending mechanism comprising:
an elongated support member;
a swivel supported at a distal end of the support member so as to swivel around an axis that intersects a longitudinal axis of the support member;
a transmitter arranged along the longitudinal axis of the support member, transmitting a driving force applied at a proximal end thereof, and making the swivel swivel relative to the support member;
a regulator regulating stress generated in the transmitter at each swivel position of the swivel relative to the support member such that the stress does not exceed a prescribed threshold; and
an actuator supplying the driving force to the transmitter,
wherein the prescribed threshold is set to a different value depending on a swivel angle of the swivel with respect to the support member,
wherein the regulator controls the driving force generated by the actuator in accordance with the swivel angle, and
wherein the transmitter comprises one or more links configured to transmit the driving force in a distal direction and in a proximal direction along the longitudinal axis of the support member.

11. A bending mechanism comprising:
an elongated support member;
a swivel supported at a distal end of the support member so as to swivel around an axis that intersects a longitudinal axis of the support member;
a transmitter arranged along the longitudinal axis of the support member, transmitting a driving force applied at a proximal end thereof, and making the swivel swivel relative to the support member; and
a regulator regulating stress generated in the transmitter at each swivel position of the swivel relative to the support member such that the stress does not exceed a prescribed threshold,
wherein the regulator includes:
an urging portion urging the transmitter at a position at a proximal end of the transmitter in a direction along the longitudinal axis to a reference position determined in accordance with a swivel angle of the swivel with respect to the support member;
a flat-plate-shaped flange fixed to a proximal end of the transmitter;
a flat-plate-shaped stopper having an identical plate thickness to the flange, being arranged next to the flange in a direction perpendicular to the longitudinal axis, and being arranged at the reference position in accordance with the swivel angle; and
a pair of pressing members arranged at positions such that the stopper and the flange are simultaneously interposed therebetween in the plate thickness direction, and
wherein the urging portion of the regulator urges the pressing members in directions such that the pressing members closely contact the stopper.

12. The bending mechanism according to claim 11, wherein when stress generated in the transmitter reaches the prescribed threshold, the regulator permits movement of the transmitter in a direction that results in the stress being reduced.

13. The bending mechanism according to claim 11, wherein the prescribed threshold is set to a different value depending on a swivel angle of the swivel with respect to the support member.

14. The bending mechanism according to claim 11, wherein the transmitter is configured to transmit the driving force in both directions along the longitudinal axis of the support member.

15. The bending mechanism according to claim 11, wherein the urging portion of the regulator is an elastic body.

16. The bending mechanism according to claim 11, wherein the urging portion of the regulator is a cylinder that generates an urging force using a fluid.

17. The bending mechanism according to claim 11, wherein the urging portion of the regulator is a magnet that generates an urging force through magnetism.

18. The bending mechanism according to claim 11, further comprising:
a support block arranged at a position such that the urging portion is interposed between the support block and the stopper and supporting an urging force; and
a cam plate changing a distance between the support block and the stopper in accordance with the swivel angle.

19. The bending mechanism according to claim 11, further comprising:
a support block arranged at a position such that the urging portion is interposed between the support block and the stopper and supporting an urging force; and
an actuator changing a distance between the support block and the stopper in accordance with the swivel angle.

* * * * *